United States Patent [19]

Iwakuma et al.

[11] Patent Number: 5,190,975
[45] Date of Patent: Mar. 2, 1993

[54] INDAN DERIVATIVES USED FOR TREATING THROMBOSES OR ASTHMA

[75] Inventors: Takeo Iwakuma, Ageo; Harumichi Kohno, Koganei; Yasuhiko Sasaki; Katsuo Ikezawa, both of Urawa; Akio Odawara, Tokyo, all of Japan

[73] Assignee: Tanabe Seiyaku Co., Ltd., Osaka, Japan

[21] Appl. No.: 897,412

[22] Filed: Jun. 12, 1992

Related U.S. Application Data

[60] Continuation-in-part of Ser. No. 688,246, Apr. 22, 1991, which is a division of Ser. No. 271,324, Nov. 15, 1988, Pat. No. 5,030,652.

[30] Foreign Application Priority Data

Nov. 18, 1987 [JP] Japan ................................ 62-290957
Jun. 21, 1988 [JP] Japan ................................ 63-152642
Jun. 21, 1988 [JP] Japan ................................ 63-152643

[51] Int. Cl.$^5$ ............................................ A61K 31/19
[52] U.S. Cl. ........................................ 514/562; 514/510; 514/602; 514/603
[58] Field of Search ................. 514/510, 562, 602, 603

[56] References Cited

U.S. PATENT DOCUMENTS 3,383,414  5/1968  Houlihan ........................... 564/79

FOREIGN PATENT DOCUMENTS 0088282  9/1983  European Pat. Off. .
63-23853  2/1988  Japan .

Primary Examiner—Jose' G. Dees
Assistant Examiner—Vera C. Clarke
Attorney, Agent, or Firm—Birch, Stewart, Kolasch & Birch

[57] ABSTRACT

Method for the treatment or prophylaxis of thromboses or asthma in warm-blooded animal which comprises administering an effective amount of a compound having the formula:

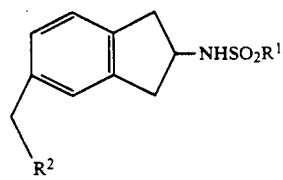

wherein $R^1$ is phenyl group or phenyl group substituted by a member selected from the group consisting of $C_1$-$C_5$ alkyl, $C_1$-$C_5$ alkoxy, halogen atom, trifluoromethyl, and nitro, or naphthyl group, and $R^2$ is hydroxymethyl or a group of the formula:

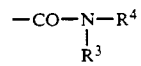

wherein $R^3$ is hydrogen atom or $C_1$-$C_5$ alkyl and $R^4$ is $C_3$-$C_6$ cycloalkyl, $C_2$-$C_6$ alkoxycarbonyl-phenyl, carboxy-phenyl, $C_1$-$C_5$ alkyl, or $C_1$-$C_5$ alkyl having a substituent selected from $C_1$-$C_5$ alkoxycarbonyl, carboxy, $C_2$-$C_6$ alkoxycarbonyl-phenyl, carboxy-phenyl, $C_2$-$C_6$ alkoxycarbonyl-($C_3$-$C_6$) cycloalkyl and carboxy-($C_3$-$C_6$) cycloalkyl, or a pharmaceutically acceptable salt thereof to said warm blooded animal.

4 Claims, No Drawings

INDAN DERIVATIVES USED FOR TREATING THROMBOSES OR ASTHMA

This invention is a continuation-in-part of U.S. Ser. No. 07/688,246 filed on Apr. 22, 1991, which is in turn a divisional application of U.S. Ser. No. 07/271,324 filed on Nov. 15, 1988, now U.S. Pat. No. 5,030,652.

FIELD OF THE INVENTION

This invention relates to novel indan derivatives and processes for the preparation thereof.

PRIOR ART

Thromboxan $A_2$ (hereinafter, referred to as "$TxA_2$") is a metabolite of arachidonic acid which exists widely in various organs of animals (e.g. liver, kidney, lung, brain, etc.) Said $TxA_2$ is known to show platelet aggregation activity and induces a variety of thrombosis such as peripheral vascular thrombosis, pulmonary embolism, coronary artery thrombosis, myocardial infarction, transient ischemia, and the like. Therefore, 4-(2-benzenesulfonylaminoethyl)phenoxyacetic acid which has $TxA_2$-antagonistic activity has been suggested to be useful for therapeutic treatment of these diseases (cf. Thrombosis Research, 35, 379-395, 1984).

SUMMARY DESCRIPTION OF THE INVENTION

As a result of various investigations, there has been found novel indan derivatives which show stronger $TxA_2$ antagonistic activity as compared with the above known compound.

Thus, the objects of the invention are to provide novel indan derivatives and a pharmaceutical composition containing the same. Another object of the invention is to provide processes for preparing said compounds. A further object of the invention is to provide novel intermediates which are useful in the synthesis of the indan derivatives of the invention. These and other objects and advantages of the invention will be apparent to those skilled in the art from the following description.

DETAILED DESCRIPTION OF THE INVENTION

This invention relates to indan derivative of the formula:

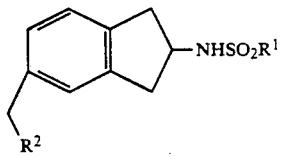

(I)

wherein $R^1$ is a substituted or unsubstituted phenyl group, naphthyl group or a sulfur-containing heterocyclic group, and $R^2$ is hydroxymethyl group or a group of the formula:

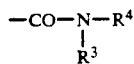

wherein $R^3$ is hydrogen atom or a lower alkyl group and $R^4$ is a cycloalkyl group, a lower alkoxycarbonyl-phenyl group, carboxy-phenyl group, a nitrogen-containing heterocyclic group, a lower alkyl group, or a lower alkyl group having a substituent selected from a lower alkoxycarbonyl group, carboxy group, a lower alkoxycarbonyl-phenyl group, carboxy-phenyl group, a lower alkoxycarbonyl-cycloalkyl group and a carboxy-cycloalkyl group, or a pharmaceutically acceptable salt thereof.

Said indan derivative and a salt thereof show potent $TxA_2$ antagonistic and/or platelet aggregation-inhibiting activities and are useful for the therapeutic treatment, amelioration and/or prophylaxis of a variety of thrombosis or emolism, coronary and cerebral vascular smooth muscle vellication, asthma, and the like.

Examples of the novel indan derivatives of the invention are those of the formula (I) wherein $R^1$ is phenyl group; a phenyl group substituted by a member selected from the group consisting of a lower alkyl group (e.g. methyl, ethyl, propyl, butyl, or pentyl), a lower alkoxy group (e.g. methoxy, ethoxy, propoxy, butoxy, or pentoxy), a halogen atom (e.g. fluorine, chlorine or bromine), trifluoromethyl, or nitro; naphthyl group; or a sulfur-containing heterocyclic group (e.g. thienyl group, etc.); $R^2$ is a hydroxymethyl group, or a group of the formula:

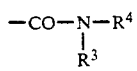

where $R^3$ is hydrogen atom or a lower alkyl group (e.g. methyl, ethyl, propyl, butyl, or pentyl), and $R^4$ is a cycloalkyl group (e.g. cyclopropyl, cyclobutyl, cyclopentyl, or cyclohexyl), a lower alkoxycarbonyl-phenyl group (e.g. methoxycarbonylphenyl, ethoxycarbonylphenyl, etc.), a carboxy-phenyl group, a nitrogen-containing heterocyclic group (e.g. tetrazolyl, etc.), a lower alkyl group (e.g. methyl, ethyl, propyl, butyl, or pentyl), or a lower alkyl group (e.g. methyl, ethyl, propyl, butyl or phentyl) having a substituent selected from a lower alkoxycarbonyl group (e.g. methoxycarbonyl, ethoxycarbonyl, propoxycarbonyl, etc.), carboxy group, a lower alkoxycarbonyl-phenyl group (e.g. methoxycarbonylphenyl, ethoxycarbonylphenyl, etc.), carboxyphenyl group, a lower alkoxycarbonyl-cycloalkyl group (e.g. methoxycarbonylcyclohexyl, etc.), and a carboxycycloalkyl group (e.g. carboxycyclohexyl group, etc.).

Among them, preferred examples of the compounds of the invention are those of the formula (I) wherein $R^1$ is phenyl, a $(C_1$-$C_5)$alkyl-phenyl, a $(C_1$-$C_5)$alkoxy-phenyl, a halogenophenyl, trifluoromethylphenyl, nitrophenyl, naphthyl, or thienyl, $R^2$ is hydroxymethyl, or a group of the formula:

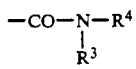

wherein $R^3$ is hydrogen atom or a $(C_1$-$C_5)$-alkyl, and $R^4$ is a $(C_3$-$C_6)$cycloalkyl, a $(C_2$-$C_6)$alkoxy-carbonyl-phenyl, carboxyphenyl, tetrazolyl, a $(C_1$-$C_5)$alkyl, or a $(C_1$-$C_5)$alkyl having a substituent selected from a $(C_2$-$C_6)$alkoxycarbonyl, carboxy, a $(C_2$-$C_6)$alkoxycarbonyl-phenyl, carboxyphenyl, a $(C_2$-$C_6)$alkoxycarbonyl-$(C_3$-$C_6)$cycloalkyl and a carboxy-$(C_3$-$C_6)$cycloalkyl.

Another preferred examples of the compounds of the invention are those of the formula (I) wherein $R^1$ is a $(C_1-C_5)$alkyl-phenyl, a $(C_1-C_5)$alkoxy-phenyl, a halogenophenyl, trifluoromethylphenyl, nitrophenyl, or naphthyl, $R^3$ is hydroxymethyl or a group of the formula:

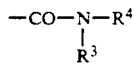

wherein $R^3$ is hydrogen atom or a $(C_1-C_5)$alkyl, and $R^4$ is carboxyphenyl, tetrazolyl, a $(C_1-C_5)$alkyl, a $(C_2-C_6)$alkoxycarbonyl$(C_1-C_5)$alkyl or a carboxy-$(C_1-C_5)$alkyl.

More preferred examples of the compounds of the invention are those of the formula (I) wherein $R^1$ is a halogenophenyl, and $R^2$ is a group of the formula:

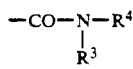

wherein $R^3$ is hydrogen atom and $R^4$ is carboxyphenyl, a $(C_2-C_4)$alkoxycarbonyl-$(C_1-C_5)$alkyl or a carboxy-$(C_1-C_5)$alkyl.

Further preferred examples of the compounds of the invention are those of the formula (I) wherein $R^1$ is chlorophenyl, and $R^2$ is a group of the formula:

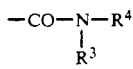

wherein $R^3$ is hydrogen atom, and $R^4$ is carboxyphenyl or a carboxy$(C_1-C_3)$alkyl.

Most preferred examples of the compounds of the invention are those of the formula (I) wherein $R^1$ is chlorophenyl, and $R^2$ is a group of the formula:

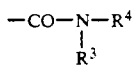

wherein $R^3$ is hydrogen atom, and $R^4$ is carboxyethyl or carboxypropyl.

The compounds (I) of the invention may exist in the form of two or four optically active isomers due to one or two asymmetric carbon atom(s), and this invention includes these optically active isomers and a mixture thereof.

According to this invention, the compounds (I) or salts thereof can be prepared by various processes as mentioned below.

Process A

The compounds (I) can be prepared by condensing a 2-aminoindan derivative of the formula:

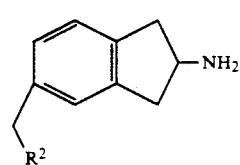

wherein $R^2$ is as defined above, or a salt thereof with a sulfonic acid compound of the formula:

wherein $R^1$ is as defined above, or a reactive derivative thereof.

The condensation reaction of the aminoindan (II) or a salt thereof (e.g. a mineral acid salt or an organic acid salt) and the sulfonic acid compound (III) or a reactive derivative thereof can be carried out in the presence or absence of an acid acceptor. The reactive derivative of the compound (III) includes any conventional reactive derivative, for example, the corresponding sulfonyl halide. The acid acceptor includes any conventional agents, for example, alkali metal carbonates, alkali metal hydrogen carbonates, trialkylamines, pyridine, and the like. The reaction is preferably carried out in a suitable solvent (e.g. water, ethyl acetate) at a temperature of 0° to 200° C.

Process B

The compounds of the formula (I) wherein $R^2$ is hydroxymethyl, i.e. the compounds of the formula (I-a):

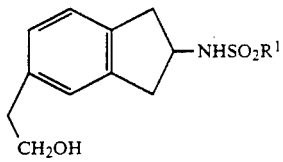

wherein $R^1$ is as defined above, can be prepared by reducing a compound of the formula:

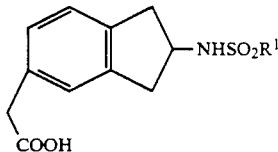

wherein $R^1$ is as defined above.

The reduction of the compound (IV) can be carried out by treating it with a reducing agent. The reducing agent includes, for example, borane 1,4-oxathiane complex. This reduction is preferably carried out in an appropriate solvent (e.g. tetrahydrofuran) at a temperature of 0° to 50° C.

Process C

The compounds of the formula (I) wherein $R^2$ is a group of the formula:

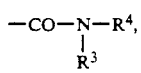

i.e. the compounds of the formula (I-b):

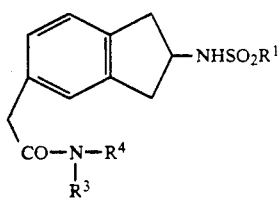 (I-b)

wherein $R^1$, $R^3$ and $R^4$ are as defined above can be prepared by condensing a compound of the formula (IV) or a reactive derivative at the carboxyl group thereof with an amine compound of the formula:

$$R^3-NH-R^4 \quad (V)$$

wherein $R^3$ and $R^4$ are as defined above or a salt thereof.

The condensation reaction of the compound (IV) or a reactive derivative at carboxyl group thereof with the amine compound (V) can be carried out by any conventional method. For example, the condensation reaction of the free carboxylic acid (IV) and the compound (V) can be carried out in the presence of a dehydrating agent. The dehydrating agent includes, for example, carbonyldiimidazole, dicyclohexylcarbodiimide, and the like. Besides, the condensation reaction of the reactive derivative at the carboxyl group of the compound (IV) with the compound (V) can be carried out in the presence or absence of an acid acceptor. A variety of the reactive derivative at the carboxyl group of the compound (IV), including, for example, acid halides, activated esters may be used for the condensation reaction. The acid acceptor includes alkali metal carbonates, alkali metal hydrogen carbonates, trialkylamines, pyridine, and the like. These reactions are preferably carried out in an appropriate solvent (e.g. tetrahydrofuran, methylene chloride) at a temperature of 0° to 50° C.

Process D

The compounds of the formula (I) wherein $R^2$ is a group of the formula:

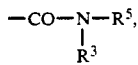

i.e. the compounds of the formula (I-c):

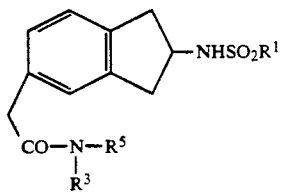 (I-c)

wherein $R^5$ is carboxy-phenyl group or a lower alkyl group having a substituent selected from carboxy group, carboxyphenyl group and a carboxy-cycloalkyl group, and $R^1$ and $R^3$ are as defined above, can be prepared by hydrolyzing a compound of the formula (I-d):

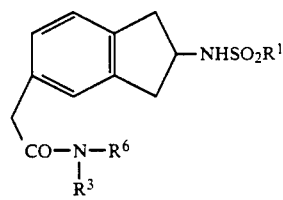 (I-d)

wherein $R^6$ is a lower alkoxycarboxy-phenyl group or a lower alkyl group having a substituent selected from a lower alkoxycarbonyl group, a lower alkoxycarboxyphenyl group and a lower alkoxycarbonyl-cycloalkyl group, and $R^1$ and $R^3$ are as defined above.

The hydrolysis of the compound (I-d) can be carried out by a conventional method, for example, by treating the compound with an alkali agent or an acid. Examples of the alkali agent are alkali metal hydroxides, and examples of the acid are mineral acids. The hydrolysis is preferably carried out in an appropriate solvent (e.g. water, a lower alcohol) at a temperature of 0° to 30° C.

All of the above reactions in Processes A to D proceed without racemization, and hence, when an optically active compounds are used as the starting materials, the desired compounds (I) can be obtained in the optically active form.

The starting compound (II) wherein $R^2$ is hydroxymethyl group can be prepared, for example, by the steps of condensing a 2-(N-protected amino)indan with a lower alkyl ester of the compound of the formula:

$$Z-CH(X)-COOH \quad (VI)$$

wherein X is a halogen atom and Z is a lower alkylmercapto group or a substituted or unsubstituted phenylmercapto group, removing the substituted mercapto group from the product to give a lower alkyl [2-(N-protected amino)indan-5-yl]acetate, hydrolyzing the product by conventional method, reducing the thus-obtained [2-[N-protected amino)indan-5-yl]acetic acid, and then removing the protecting group from the product by conventional method.

On the other hand, the compound (II) wherein $R^2$ is a group of the formula:

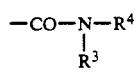

can be prepared, for example, by the steps of
(a) condensing a 2-(N-protected amino)indan with a compound of the formula:

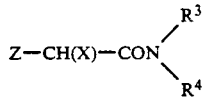 (VII)

wherein $R^3$, $R^4$, X and Z are as defined above, removing the substituted mercapto group from the product to give a compound of the formula:

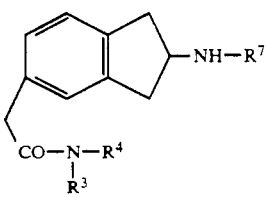

(VIII)

wherein R⁷ is a protecting group and R³ and R⁴ are as defined above, or (b) condensing a [2-(N-protected amino)indan-5-yl]acetic acid or a reactive derivative thereof with the amine compound (V) to give the compound (VIII), and (c) removing the protecting group from the compound (VIII) by conventional method.

Further, the starting compound (IV) can be prepared, for example, by the steps of removing the protecting group from a lower alkyl [2-(N-protected amino)indan-5-yl]acetate, condensing the product with the sulfonic acid compound (III) or a reactive derivative thereof, and hydrolyzing the product by conventional method.

The condensation reaction of the 2-(N-protected amino)indan with the compound (VI) or (VII) can be carried out in an appropriate solvent in the presence of Lewis acid (e.g., stannic chloride, aluminum chloride) under cooling. The amino-protecting group includes any conventional protecting groups, for example, acyl groups such as benzyloxycarbonyl, formyl, a lower alkoxycarbonyl group. The removal of the substituted mercapto group from the resulting condensation product can be carried out by heating it under an acidic condition in the presence of a heavy metal (e.g. zinc, iron), or by heating in hydrogen atmosphere in the presence of a catalyst such as Raney nickel in an alcohol solvent. On the other hand, the reduction of the [2-(N-protected amino]indan-5-yl]acetic acid, the condensation reaction of the [2-(N-protected amino)indan-5-yl]acetic acid or a reactive derivative thereof with the amine compound (V) and the condensation reaction of the lower alkyl (2-aminoindan-5-yl)acetate with the sulfonic acid compound (III) or a reactive derivative thereof can be carried out in the same manner as described in either one of Processes (A) to (D).

The compounds (I) of this invention can be used for pharmaceutical use either in the form of a free base or a salt. For the pharmaceutical use, the salt of the compounds is preferably pharmaceutically acceptable salts, for example, inorganic or organic acid salts such as alkali metal salts (e.g. sodium salt, potassium salt), alkaline earth metal salts (e.g. calcium salt, magnesium salt), heavy metal salts (e.g. zinc salt), ammonium salt, organic amine salts (e.g. triethylamine salt, pyridine salt, ethanolamine salt, a basic amino acid salt), and the like. These salts may readily be prepared by treating the compounds (I) with the corresponding inorganic or organic base in an appropriate solvent.

The compounds (I) or a salt thereof may be administered either orally or parenterally and may also be used in the form of a pharmaceutical preparation containing the same compound in admixture with pharmaceutical excipients suitable for oral or parenteral administration. The pharmaceutical preparations may be in solid form such as tablets, capsules and powders, or in liquid form such as solutions, suspensions or emulsions. Moreover, when administered parenterally, it may be used in the form of injections.

As mentioned hereinbefore, the compounds (I) or a salt thereof of this invention show potent $TxA_2$ antagonistic activity and hence are useful as platelet aggregation-inhibiting agent and are also useful for the treatment, amelioration and/or prophylaxis of a variety of thrombosis or embolism, such as cerebral thrombosis, coronary artery thrombosis, pulmonary thrombosis, pulmonary embolism, peripheral vascular embolism, thromboangiitis, and the like. Moreover, the compounds (I) or a salt thereof are useful for the treatment, amelioration and/or prophylaxis of myocardial ischemia, unstable angina pectoris, coronary vellication, cerebral blood vessl vellication after subarachnoid hemorrhage, cerebral hemorrhage, asthma, and the like. Besides, although some known $TxA_2$ antagonists show excellent $TxA_2$ antagonistic activity but at the same time show transient $TxA_2$-like activity and hence has side effects such as platelet aggregation-inducing activity, broncho-constriction activity, blood vessel constriction activity, the compounds (I) of this invention do not show such $TxA_2$-like activity when administered either orally or parenterally.

Throughout the specification and claims, the term "lower alkyl", "lower alkoxy" and "cycloalkyl" should be interpreted as referring to alkyl having 1 to 5 carbon atoms, alkoxy having 1 to 5 carbon atoms, and cycloalkyl having 3 to 6 carbon atoms, respectively.

The pharmacological activity and processes for the preparation of the compounds of this invention are illustrated by the following Experiments, Examples and Reference Examples.

EXPERIMENT

Inhibiting effect on arachidonic acid-induced pulmonary embolism (in vivo):

A test compound in an aqueous carboxymethylcellulose solution (20 ml/kg) was orally administered to ddy-male mice fasted overnight. Three hours later, arachidonic acid (125 mg/kg) was injected to the tail vein of mice to induce pulmonary embolism, and the recovery time (minute) of locomotive activity of the mice was compared with that of a control group of mice to which a 0.25% aqueous CMC solution was administered instead of the test compound solution. The inhibiting effect of each test compound on arachidonic acid-induced pulmonary embolism was estimated in terms of the dose required to shorten the recovery time by at least 15% as compared with the control group. The results are shown in Table 1.

TABLE 1

| Test compound No.* | Inhibiting effect on arachidonic acid-pulmonary embolism (in vivo) (mg/kg) |
|---|---|
| Compounds of this invention | |
| 1 | 0.03 |
| 2 | 0.03 |
| Control | 30 |

*Chemical name of test compounds are as follows.

| Compd. No. | Chemical name |
|---|---|
| 1: | Sodium 3-[[2-[(4-chlorophenyl)sulfonylamino]-indan-5-yl]acetylamino]-n-propionate |
| 2: | Sodium 4-[[2-[(4-chlorophenyl)sulfonylamino]-indan-5-yl]acetylamino]-n-butyrate |
| Control: | 4-(2-Benzensulfonylaminoethyl)phenoxyacetic acid (a compound disclosed in Thrombosis Research, 35, 379–395, 1984) |

EXAMPLE 1

(1) (2-Formylaminoindan-5-yl)acetic acid (219 mg) and carbonyldiimidazole (162 mg) are mixed with stirring in a mixed solvent of tetrahydrofuran-methylene chloride under ice cooling and the mixture is stirred at room temperature for one hour, and to the reaction mixture are added methyl β-aminopropionate hydrochloride (140 mg) and triethylamine (100 mg), and the mixture is stirred at room temperature for 2 hours. After the reaction, methanol is added to the mixture, and the solvent is distilled off under reduced pressure. The residue is separated and purified by silica gel column chromatography (solvent, chloroform - methanol=19:1) and then recrystallized from ethyl acetate - n-hexane to give methyl 3-[(2-formylaminoindan-5-yl)acetylamino]-n-propionate (238 mg) m.p. 108°–110° C.

(2) The above product (200 mg) is dissolved in 5% methanol-hydrochloric acid, and the mixture is stirred at room temperature for 24 hours. After the reaction, the solvent is distilled off, and the residue is recrystallized from methanol - diethyl ether to give methyl 3-[(2-aminoindan-5-yl)acetylamino]-n-propionate hydrochloride (152 mg) as colorless needles. m.p. 195°–197° C.

(3) A mixture of the free base of the above product (138 mg), 4-chlorophenylsulfonyl chloride (106 mg), potassium carbonate (138 mg) and ethyl acetate (10 ml) - water (5 ml) is stirred at room temperature for one hour. After the reaction, the organic layer is taken, washed, dried, and then distilled to remove the solvent. The residue is recrystallized from ethyl acetate - n-hexane to give methyl 3-[[2-[(4-chlorophenyl)sulfonylamino]indan-5-yl]acetylamino]-n-propionate (200 mg).

m.p. 147°–150° C.,
MS (m/e): 450 (M+),
IR $\nu_{max}^{nujol}$ cm$^{-1}$: 3380, 1715, 1650

EXAMPLE 2

(1) In the same manner as described in Example 1-(1), (2-formylaminoindan-5-yl)acetic acid (2.20 g) and methyl γ-aminobutyrate are reacted to give methyl 4-[(2-formylaminoindan-5-yl)acetylamino]-n-butyrate (2.57 g).

m.p. 89°–93° C.

(2) The above product (187 mg) is treated in the same manner as described in Example 1-(2) to give methyl 4-[(2-aminoindan-5-yl)acetylamino]-n-butyrate hydrochloride (165 mg).

m.p. 198°–200° C.

(3) The above product (425 mg) and 4-chlorophenylsulfonyl chloride (276 mg) are treated in the same manner as described in Example 1-(3) to give methyl 4-[[2-[(4-chlorophenyl)sulfonylamino]indan-5-yl]acetylamino]-n-butyrate (571 mg).

m.p. 128°–129° C. (recrystallized from ethyl acetate-n-hexane)
MS (m/e): 464 (M+)
IR $\nu_{max}^{nujol}$ cm$^{-1}$: 3360, 3280, 1735, 1720, 1650

EXAMPLE 3

(1) In the same manner as described in Example 1-(1), 2-(benzyloxycarbonylamino)indan-5-acetic acid and methyl γ-aminobutyrate are reacted to give methyl 4-[(2-benzyloxycarbonylaminoindan-5-yl)acetylamino]-n-butyrate.

m.p 128°–130° C.

(2) The above product (917 mg) is dissolved in a mixture of tetrahydrofuran—water, and is subjected to catalytic reduction in the presence of 10% palladium-carbon under atmospheric pressure at room temperature. Two hours later, the catalyst (200 mg) is further added, and the mixture is further reacted for one hour. After the catalyst is filtered off, the filtrate is distilled. The residue is treated with methanol-hydrogen chloride to give hydrochloride of the product, which is recrystallized from methanol - isopropyl alcohol - isopropyl ether to give methyl 4-[(2-aminoindan-5-yl)acetylamino]-n-butyrate hydrochloride (518 mg) as colorless needles. m.p. 200°–201° C.

(3) The above product is treated in the same manner as described in Example 1-(3) to give methyl 4-[[2-[(4-chlorophenyl)sulfonylamino]indan-5-yl]acetylamino]-n-butyrate.

m.p. 128°–129° C. (recrystallized from ethyl acetate-n-hexane)
MS (m/e): 464 (M+)

EXAMPLE 4

(1) To a solution of 2-formylaminoindan (3.22 g) and methyl 3-[chloro(phenylthio)acetylamino]-n-propionate (6.04 g) in methylene chloride is added dropwise a solution of stannic chloride (15.6 g) in methylene chloride at −3° to −1° C., and the mixture is stirred at room temperature for 5 hours. The reaction mixture is poured into water, and thereto is added chloroform. The organic layer is separated, washed and dried and then concentrated under reduced pressure. The residue is separated and purified by silica gel column chromatography (solvent, ethyl acetate) to give methyl 3-[(2-formylaminoindan-5-yl)(phenylthio)acetylamino]-n-propionate (5.21 g) as colorless oil.

IR $\nu_{max}^{nujol}$ cm$^{-1}$: 3290, 1735, 1650

(2) To a solution of the above product (3.1 g) in acetic acid is added zinc dust (9.8 g), and the mixture is refluxed with stirring for 2 hours. After cooling, zinc dust is removed by filtration, and the solvent is distilled off, and the residue is dissolved in chloroform. The solution is washed with saturated aqueous saline solution, dried, and then the solvent is distilled off. The residue is separated and purified by silica gel column chromatography (solvent, chloroform:methanol=19:1) and recrystallized from ethyl acetate - n-hexane to give methyl 3-[(2-formylaminoindan-5-yl)acetylamino]-n-propionate (1.54 g) as colorless crystals. m.p. 108°–110° C.

(3) To a solution of the above product (2 g) in methanol is added 5% hydrochloric acid—methanol, and the mixture is reacted at room temperature for 24 hours. The solvent is distilled off from the reaction mixture, and the residue is crystallized from isopropyl ether—diethyl ether to give methyl 3-[(2-aminoindan-5-yl)acetylamino]-n-propionate hydrochloride (1.52 g) as colorless needles.

m.p. 195°–197° C.

(4) The free base of the above product (2.76 g) is added to a mixture of ethyl acetate (200 ml) and saturated aqueous sodium hydrogen carbonate solution (100 ml) with stirring, and thereto is further added 4-chlorophenylsulfonyl chloride (2.11 g), and the mixture is stirred at room temperature for 1.5 hour. The ethyl acetate layer is separated, dried, and then the solvent is distilled off under reduced pressure. The residue is crystallized from ethyl acetate - n-hexane to give methyl 3-[[2-[(4-chlorophenyl)sulfonylamino]indan-5- yl]acetylamino]-n-propionate (4.06 g) as colorless needles. m.p. 147°–150° C.

EXAMPLE 5

To a solution of methyl 4-[(phenylthio)acetylamino]-n-butyrate (6.42 g) in methylene chloride (20 ml) is added dropwise a solution of sulfuryl chloride (3.42 g) in methylene chloride (10 ml). Said dropwise addition is carried out under argon atmosphere with ice-cooling for 10 minutes. The mixture is stirred at the same temperature for one hour. The solvent is distilled off, and the residue is dissolved in methylene chloride (40 ml). 2-Formylaminoindan (3.22 g) is added to the solution and a solution of stannic chloride (11.5 g) and nitromethane (2.75 g) in methylene chloride (20 ml) are added thereto below 10° C. for 15 minutes, and the mixture is stirred at room temperature for 8 hours. After the reaction, water (30 ml) is added to the mixture, and the mixture is stirred for 20 minutes. Chloroform (30 ml) is added to the mixture, and the mixture is washed with 10% hyrochloric acid and dried. The solvent is distilled off, and the residue is dissolved in acetic acid (50 ml). Zinc dust (1.3 g) is added to the solution under reflux, and the mixture is refluxed for 15 minutes. After cooling, zinc dust is removed by filtration, and the solvent is distilled off, and the residue is dissolved in chloroform (100 ml). The solution is washed with an aqueous saline solution containing potassium carbonate (1 g), dried, and then the solvent is distilled off. Ethyl acetate (30 ml) is added to the residue, and the mixture is extracted with water. The solvent is distilled off, and 12.5% hydrogen chloride-methanol solution (80 ml) is added to the residue, and the mixture is stirred at room temperature for 17.5 hours. The solvent is distilled off, and the residue is dissolved in a mixture of water (30 ml) and toluene (25 ml). Potassium carbonate (5.03 g) and 4-chlorophenylsulfonyl chloride (3.39 g) are added to the solution, and the mixture is stirred. After the reaction, the mixture is extracted with a mixture of ethyl acetate and tetrahydrofuran, and the extract is washed with an aqueous saline solution, and dried. The solvent is distilled off, and the residue is recrystallized from a mixture of methanol and ethere to give methyl 4-[[2-[(4-chlorophenyl)-sulfonylamino]-indan-5-yl]acetylamino]-n-butyrate (4.53 g) as colorless powder.

m.p. 126.5°–127.5° C.

EXAMPLES 6 TO 23

In the same manner as described in any one of Examples 1 to 5, the corresponding starting compounds are treated to give the compounds of the following Table 2.

TABLE 2

(A)

Compound A structure: indan ring with $-NHSO_2-R^1$ at the 2-position and $-CO-N(R^3)-R^4$ substituent via $CH_2$.

| Ex. No. | R¹ | R³ | R⁴ | Physical properties, etc. |
|---|---|---|---|---|
| 6 | 4-Cl-C₆H₄- | H | —CH₂CO₂CH₃ | MS (m/e): 436 (M⁺)<br>IR $\nu_{max}^{nujol}$ cm⁻¹: 1745, 1670 |
| 7 | " | H | 4-(CO₂C₂H₅)-C₆H₄- | m.p. 199.5–200.5° C. (recryst. from THF-hexane)<br>MS (m/e): 512 (M⁺)<br>IR $\nu_{max}^{nujol}$ cm⁻¹: 3260, 1710, 1670 |
| 8 | " | H | cyclohexyl | m.p. 203–204° C. (recryst. from THF-isopropyl ether)<br>MS (m/e): 446 (M⁺)<br>IR $\nu_{max}^{nujol}$ cm⁻¹: 3350, 3130, 1670 |
| 9 | " | CH₃ | —CH₃ | m.p. 146.5–148° C. (recryst. from isopropanol-isopropyl ether)<br>MS (m/e): 392 (M⁺)<br>IR $\nu_{max}^{nujol}$ cm⁻¹: 3180, 1630 |
| 10 | 4-Cl-C₆H₄- | H | —C₂H₅ | m.p. 148–150° C. (recryst. from ethanol-n-hexane)<br>MS (m/e): 392 (M⁺)<br>IR $\nu_{max}^{nujol}$ cm⁻¹: 3310, 3270, 1640 |
| 11 | " | H | —CH(CH₃)₂ | m.p. 165–166° C. (recryst. from ethanol-n-hexane)<br>MS (m/e): 406 (M⁺)<br>IR $\nu_{max}^{nujol}$ cm⁻¹: 3360, 3080, 1640 |
| 12 | " | H | —C(CH₃)₃ | m.p. 148–149° C. (recryst. from ethanol-n-hexane)<br>MS (m/e): 420 (M⁺) |

TABLE 2-continued

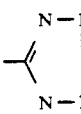

(A)

| Ex. No. | R[1] | R[3] | R[4] | Physical properties, etc. |
|---|---|---|---|---|
| | | | | IR $\nu_{max}^{nujol}$ cm$^{-1}$: 3380, 3180, 1650 |
| 13 | " | H | 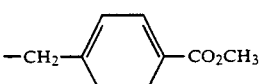 | m.p. 263-264° C. (recryst. from ethyl acetate) MS (m/e): 433 (M$^+$ + 1) IR $\nu_{max}^{nujol}$ cm$^{-1}$: 3260, 3220, 1700, 1625 Sodium salt: m.p. 204-209° C. (dec.) |
| 14 | " | H | 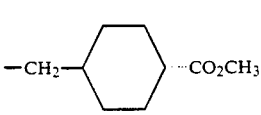 | m.p. 151-153.5° C. (recryst. from ethyl acetate-n-hexane) MS (m/e): 515 (M$^+$ + 3) IR $\nu_{max}^{nujol}$ cm$^{-1}$: 3215, 3150, 1730, 1720, 1635 |
| 15 | " | H | 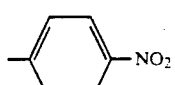 | m.p. 147-150° C. (recryst. from ethyl acetate-n-hexane) MS (m/e): 521 (M$^+$ + 3) IR $\nu_{max}^{nujol}$ cm$^{-1}$: 3360, 3160, 1735, 1640 |
| 16 | 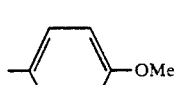 | H | —(CH$_2$)$_2$CO$_2$CH$_3$ | m.p. 121-123° C. (recryst. from ethyl acetate-iso-propyl ether) MS (m/e): 462 (M$^+$ + 1) IR $\nu_{max}^{nujol}$ cm$^{-1}$: 3260, 3100, 1740, 1640, 1530, 1450, 1160 |
| 17 | 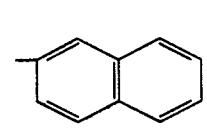 | H | —(CH$_2$)$_2$CO$_2$CH$_3$ | m.p. 115-116° C. (recryst. from methanol-ethyl ether) MS (m/e): 447 (M$^+$ + 1) IR $\nu_{max}^{nujol}$ cm$^{-1}$: 3390, 3170, 1720, 1650 |
| 18 |  | H | " | m.p. 121-122° C. (recryst. from ethyl acetate-n-hexane) MS (m/e): 467 (M$^+$ + 1) IR $\nu_{max}^{nujol}$ cm$^{-1}$: 3330, 3270, 1730, 1645 |
| 19 | 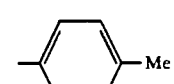 | H | " | m.p. 76-78° C. (recryst. from ethyl acetate) MS (m/e): 423 (M$^+$ + 1) IR $\nu_{max}^{nujol}$ cm$^{-1}$: 3380, 3130, 1740, 1650 |
| 20 | 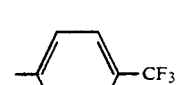 | H | —(CH$_2$)$_3$CO$_2$CH$_3$ | m.p. 127-128° C. (recryst. from ethyl acetate-n-hexane) MS (m/e): 445 (M$^+$ + 1) IR $\nu_{max}^{nujol}$ cm$^{-1}$: 3320, 3260, 1730, 1650 |
| 21 |  | H | —(CH$_2$)$_3$CO$_2$CH$_3$ | m.p. 129-130° C. (recryst. from ethyl acetate-iso-propyl ether) MS (m/e): 499 (M$^+$ + 1) IR $\nu_{max}^{nujol}$ cm$^{-1}$: 3370, 3140, 1730, 1643 |

TABLE 2-continued

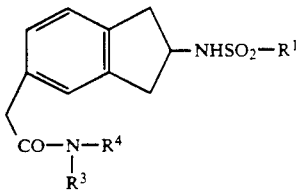

(A)

| Ex. No. | Compound A R¹ | R³ | R⁴ | Physical properties, etc. |
|---|---|---|---|---|
| 22 | ⟨benzene⟩—Br | H | " | m.p. 118–120° C. (recryst. from ethyl acetate-n-hexane) MS (m/e): 511 ($M^+ + 3$) and 509 ($M^+ + 1$) IR $\nu_{max}^{nujol}$ cm$^{-1}$: 3360, 3295, 3150 (sh), 3090, 1722, 1650 |
| 23 | ⟨benzene⟩ | H | " | m.p. 95–99° C. (recryst. from ethyl acetate-n-hexane) MS (m/e): 431 ($M^+$) IR $\nu_{max}^{nujol}$ cm$^{-1}$: 3260, 3170, 3090, 1720 |

EXAMPLE 24

(1) A mixture of methyl (2-aminoindan-5-yl)acetate hydrochloride (2.43 g), potassium carbonate (5.52 g), water (60 ml), ethyl acetate (60 ml) and 4-chlorophenylsulfonyl chloride (2.11 g) is stirred at room temperature for one hour. The ethyl acetate layer is separated from the reaction mixture, washed with aqueous saline solution, dried, and distilled under reduced pressure to remove the solvent. The resulting crude product is recrystallized from a mixture of ethyl acetate and n-hexane to give methyl [2-[(4-chlorophenyl)sulfonylamino]indan-5-yl]acetate (3.02 g).

m.p. 91°–92° C.
MS (m/e): 381 ($M^+ +2$), 379 ($M^+$)
IR $\nu_{max}^{nujol}$ cm$^{-1}$: 3620, 1725

(2) To a solution of the above product (3.0 g) in methanol (40 ml) is added 1N aqueous sodium hydroxide (20 ml), and the mixture is stirred at room temperature for one hour and distilled under reduced pressure to remove the solvent. The residue is dissolved in water and adjusted to about pH 1 with 10% hydrochloric acid and then extracted with ethyl acetate. The extract is dried and distilled under reduced pressure to remove the solvent. The resulting crude product is recrystallized from a mixture of ethyl acetate and n-hexane to give [2-[(4-chlorophenyl)sulfonylamino]indan-5-yl]acetic acid (2.82 g) as colorless crystals.

m.p. 159°–161° C.
MS (m/e): 174 ($M^+$- 191)
IR $\nu_{max}^{nujol}$ cm$^{-1}$: 3280, 1700

(3) The above product (915 mg), thionyl chloride (2 ml), tetrahydrofuran (20 ml) and methylene chloride (20 ml) are mixed, and the mixture is refluxed with stirring for 2 hours. After the reaction, the solvent is distilled off under reduced pressure. The residue is dissolved in methylene chloride (10 ml), and the solution is added dropwise to a mixture of methyl 3-aminopropionate hydrochloride (523 mg), triethylamine (760 mg) and methylene chloride (10 ml) on an ice bath. After stirring the mixture at room temperature for 3 hours, the reaction mixture is distilled under reduced pressure to remove the solvent. The residue is extracted with ethyl acetate, and the extract is washed with 10% hydrochloric acid, aqueous sodium hydrogen carbonate solution and saline solution in this order, dried and then distilled under reduced pressure to remove the solvent. The resulting crude crystals are recrystallized from methylene chloride and n-hexane to give methyl 3-[[2-(4-chlorophenyl)sulfonylamino]indan-5-yl]acetylamino]-n-propionate (962 mg)

m.p. 147°–150° C.
MS (m/e): 450 ($M^+$)
IR $\nu_{max}^{nujol}$ cm$^{-1}$: 3380, 1715, 1650

EXAMPLES 25 TO 32

(1) In the same manner as described in Example 24-(1), the corresponding starting compounds are treated to give the compounds of the following Table 3.

TABLE 3

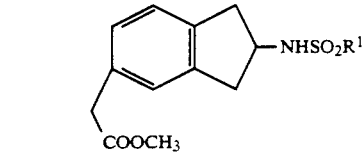

(B)

| Compound B R¹ | Physical properties, etc. |
|---|---|
| ⟨benzene⟩ | m.p. 92–93.5° C.*1 MS (m/e): 345 ($M^+$) IR $\nu_{max}^{nujol}$ cm$^{-1}$: 3300, 1725 |
| ⟨benzene⟩—CH₃ | m.p. 102–104° C.*1 MS (m/e): 359 ($M^+$) IR $\nu_{max}^{nujol}$ cm$^{-1}$: 3280, 1740 |

TABLE 3-continued

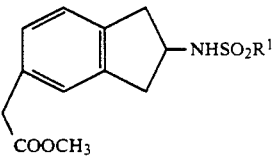
(B)

Compound B

| R¹ | Physical properties, etc. |
|---|---|
| 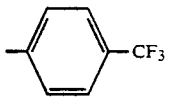 -CF₃ | m.p. 111-112° C.*1<br>MS (m/e): 413 (M⁺)<br>IR $\nu_{max}^{nujol}$ cm⁻¹: 3290, 1740 |
| 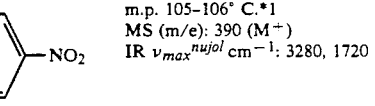 -NO₂ | m.p. 105-106° C.*1<br>MS (m/e): 390 (M⁺)<br>IR $\nu_{max}^{nujol}$ cm⁻¹: 3280, 1720 |
| 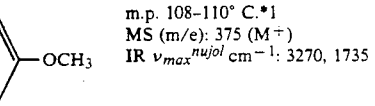 -OCH₃ | m.p. 108-110° C.*1<br>MS (m/e): 375 (M⁺)<br>IR $\nu_{max}^{nujol}$ cm⁻¹: 3270, 1735 |
| 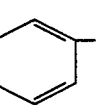 | m.p. 85-87° C.*1<br>MS (m/e): 395 (M⁺)<br>IR $\nu_{max}^{nujol}$ cm⁻¹: 3270, 1730 |
| 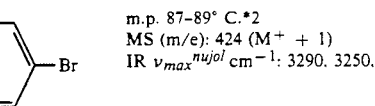 -Br | m.p. 87-89° C.*2<br>MS (m/e): 424 (M⁺ + 1)<br>IR $\nu_{max}^{nujol}$ cm⁻¹: 3290, 3250, 1720 |
| 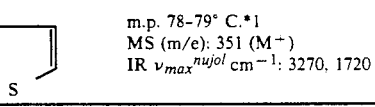 S | m.p. 78-79° C.*1<br>MS (m/e): 351 (M⁺)<br>IR $\nu_{max}^{nujol}$ cm⁻¹: 3270, 1720 |

*1 Recrystallized from ethyl acetate-n-hexane
*2 Recrystallized from isopropanol-n-hexane-isopropyl ether (2) In the same manner as described in Example 24-(2), the products obtained in Paragraph (1) are treated to give the compounds of the following Table 4.

TABLE 4

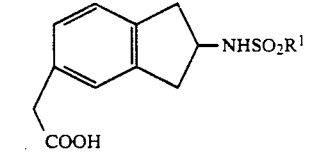
(C)

Compound C

| R¹ | Physical properties, etc. |
|---|---|
| 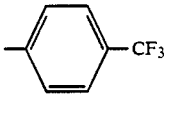 | m.p. 123-125° C.*3<br>MS (m/e): 331 (M⁺)<br>IR $\nu_{max}^{nujol}$ cm⁻¹: 3550, 3240 |
| 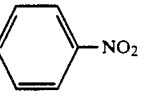 -CH₃ | m.p. 140-141° C.*1<br>MS (m/e): 345 (M⁺)<br>IR $\nu_{max}^{nujol}$ cm⁻¹: 3280, 1690 |

TABLE 4-continued

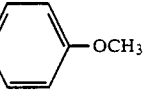
(C)

Compound C

| R¹ | Physical properties, etc. |
|---|---|
| 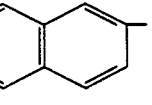 -CF₃ | m.p. 161-162° C.*1<br>MS (m/e): 399 (M⁺)<br>IR $\nu_{max}^{nujol}$ cm⁻¹: 3265, 1695 |
| 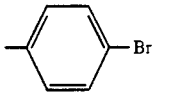 -NO₂ | m.p. 173-174° C.*1<br>MS (m/e): 376 (M⁺)<br>IR $\nu_{max}^{nujol}$ cm⁻¹: 3285, 1700 |
| 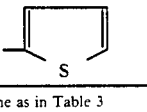 -OCH₃ | m.p. 154-155° C.*1<br>MS (m/e): 361 (M⁺)<br>IR $\nu_{max}^{nujol}$ cm⁻¹: 3270, 1690 |
| 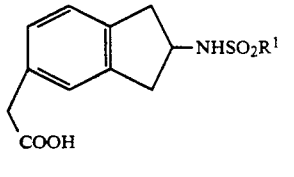 | m.p. 153-155° C.*1<br>MS (m/e): 381 (M⁺)<br>IR $\nu_{max}^{nujol}$ cm⁻¹: 3270, 1705 |
| 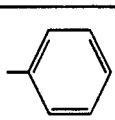 -Br | m.p. 167-168.5° C.*1<br>MS (m/e): 410 (M⁺ + 1)<br>IR $\nu_{max}^{nujol}$ cm⁻¹: 3265, 1698 |
| 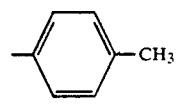 S | m.p. 104-106° C.*1<br>MS (m/e): 337 (M⁺)<br>IR $\nu_{max}^{nujol}$ cm⁻¹: 3280, 1705 |

*1 The same as in Table 3
*3 Recrystallized from diethyl ether-n-hexane (3) In the same manner as described in Example 24-(3), the products obtained in Paragraph (2) and methyl 3-aminopropionate (or methyl 4-aminobutyrate) are treated to give the same compounds as in Examples 16 to 23.

EXAMPLE 33

A mixture of methyl 3-[[2-[(4-chlorophenyl)sulfonylamino]indan-5-yl]acetylamino]-n-propionate (720 mg), 1N aqueous sodium hydroxide (3 ml) and methanol (10 ml) is stirred at room temperature for 3 hours and then, the solvent is distilled off under reduced pressure. The residue is dissolved in water, and the solution is adjusted to pH 1 with 10% hydrochloric acid and is extracted with ethyl acetate. The extract is washed with aqueous saline solution, dried and then distilled under reduced pressure to remove the solvent. The resulting crude crystals are recrystallized from ethyl acetate - n-hexane to give 3-[[2-[(4-chlorophenyl)sulfonylamino]indan-5-yl]acetylamino]-n-propionic acid (656 mg, yield 94%) as colorless crystals.

m.p. 150°-153° C.
MS (m/e): 245 (M+- 191)
IR $\nu_{max}^{nujol}$ cm⁻¹: 3320, 3270, 1700, 1650
Sodium salt: m.p. 185°-187° C.

EXAMPLES 34 TO 46

In the same manner as described in Example 33, the products obtained in Examples 2, 6, 7 and 14 to 23 are treated to give the compounds of the following Table 5.

TABLE 5 (D)

Compound D structure: indane core with —NHSO$_2$—R$^1$ at 2-position and —CH$_2$—CO—N(R$^3$)—R$^5$ at 5-position.

| Ex. No. | R$^1$ | R$^3$ | R$^5$ | Physical properties, etc. |
|---|---|---|---|---|
| 34 | 4-Cl-C$_6$H$_4$— | H | —CH$_2$CO$_2$H | m.p. 182–185° C. (recryst. from ethyl acetate)<br>MS (m/e): 231 (M$^+$ − 191)<br>IR $\nu_{max}^{nujol}$ cm$^{-1}$: 3390, 3265, 1720, 1615<br>Sodium salt:<br>m.p. 250–253° C. (dec.) |
| 35 | " | H | —(CH$_2$)$_3$CO$_2$H | m.p. 123.5–125.5° C. (recryst. from THF-isopropyl ether)<br>MS (m/e): 450 (M$^+$)<br>IR $\nu_{max}^{nujol}$ cm$^{-1}$: 3270, 3160, 1700, 1620, 1150<br>Sodium salt:<br>m.p. 196.1° C. (dec.) |
| 36 | " | H | 4-HO$_2$C-C$_6$H$_4$— | m.p. 258.5–260.5° C. (recryst. from THF-isopropyl ether)<br>MS (m/e): 485 (M$^+$ + 1)<br>IR $\nu_{max}^{nujol}$ cm$^{-1}$: 3320, 1670<br>Sodium salt:<br>m.p. 305–311° C. (dec.) |
| 37 | " | H | —CH$_2$—C$_6$H$_4$—CO$_2$H (4-) | m.p. 227.5–229.5° C.<br>MS (m/e): 501 (M$^+$ + 3)<br>IR $\nu_{max}^{nujol}$ cm$^{-1}$: 3300, 2400–2800, 1700, 1682, 1640 |
| 38 | 4-Cl-C$_6$H$_4$— | H | —CH$_2$—(cyclohexyl)—CO$_2$H | m.p. 190–191.5° C. (dec.)<br>MS (m/e): 507 (M$^+$ + 3)<br>IR $\nu_{max}^{nujol}$ cm$^{-1}$: 3360, 3140, 3090, 1700, 1640<br>Sodium salt:<br>m.p. >280° C. |
| 39 | 4-NO$_2$-C$_6$H$_4$— | H | —(CH$_2$)$_2$CO$_2$H | m.p. 159–161° C. (recryst. from THF-isopropyl ether)<br>MS (m/e): 448 (M$^+$ + 1)<br>IR $\nu_{max}^{nujol}$ cm$^{-1}$: 3350, 3100, 1710, 1650, 1530, 1450, 1340, 1160<br>Sodium salt:<br>m.p. 192–196° C. (dec.) |
| 40 | 4-MeO-C$_6$H$_4$— | H | " | foam<br>MS (m/e): 433 (M$^+$ + 1)<br>IR $\nu_{max}^{nujol}$ cm$^{-1}$: 3270, 1710, 1650 |
| 41 | 2-naphthyl | H | " | foam<br>MS (m/e): 453 (M$^+$ + 1)<br>IR $\nu_{max}^{nujol}$ cm$^{-1}$: 3260, 1710, 1640 |
| 42 | 2-thienyl | H | " | m.p. 87–89° C. (recryst. from ethyl acetate)<br>MS (m/e): 409 (M$^+$ + 1)<br>IR $\nu_{max}^{nujol}$ cm$^{-1}$: 3390, 3120, 1710, 1650 |

TABLE 5-continued

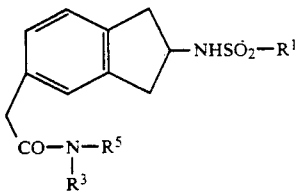

(D)

| Ex. No. | Compound D R¹ | R³ | R⁵ | Physical properties, etc. |
|---|---|---|---|---|
| 43 | ⟨benzene⟩—CH₃ | H | —(CH₂)₃CO₂H | m.p. 118–119° C. (recryst. from isopropyl alcohol-isopropyl ether) MS (m/e): 431 (M⁺ + 1) IR $\nu_{max}^{nujol}$ cm⁻¹: 3280, 3180, 1700, 1620 Sodium salt: m.p. 166–168° C. |
| 44 | ⟨benzene⟩—CF₃ | H | —(CH₂)₃CO₂H | m.p. 150–152° C. (recryst. from ethanol-n-hexane) MS (m/e): 485 (M⁺ + 1) IR $\nu_{max}^{nujol}$ cm⁻¹: 3320, 3280, 1720, 1650 Sodium salt: m.p. 197–199° C. |
| 45 | ⟨benzene⟩—Br | H | " | m.p. 122.5–125° C. (recryst. from isopropanol-ethyl ether-water) MS (m/e): 497 (M⁺ + 3), 495 (M⁺ + 1) IR $\nu_{max}^{nujol}$ cm⁻¹: 3270, 3170, 3090, 1698 Sodium salt: m.p. 197–200° C. |
| 46 | ⟨benzene⟩ | H | " | m.p. 128–131° C. (recryst. from isopropanol-ethyl acetate-ethyl ether) MS (m/e): 417 (M⁺ + 1) IR $\nu_{max}^{nujol}$ cm⁻¹: 3270, 3170, 3080, 1700 Sodium salt: m.p. 153–157° C. |

EXAMPLE 47

In the same manner as described in Examples 24 and 33, methyl (2-aminoindan-5-yl)acetate hydrochloride, 4-chlorophenylsulfonyl chloride and methyl N-methyl-β-aminopropionate hydrochloride are treated to give 2-[N-[2-[(4-chlorophenyl)sulfonylamino]indan-5-yl]acetyl-N-methylamino]acetic acid.

MS (m/e): 436 (M⁺)
IR $\nu_{max}^{nujol}$ (cm⁻¹): 3500, 3200, 1720, 1630
Sodium salt: m.p. 204°–205° C. (dec.)

EXAMPLE 48

A mixture of [2-(4-chlorophenyl)sulfonylamino]indan-5-yl]acetic acid (987 mg), thionyl chloride (2 ml), tetrahydrofuran (10 ml) and methylene chloride (10 ml) is refluxed for 2 hours. After the reaction, the solvent is distilled off under reduced pressure. The residue is dissolved in tetrahydrofuran (8 ml) (this solution is hereinafter referred to as "Solution A"). Separately, to a mixture of 5-aminovaleric acid (326 mg), diethyl ether (5 ml), 0.6N aqueous sodium hydroxide (5 ml) and ethanol (20 ml) are added dropwise Solution A and 0.6N aqueous sodium hydroxide (5 ml) under ice cooling with stirring, and the mixture is stirred at room temperature overnight. After the reaction, diethyl ether and water are added to the reaction mixture. The aqueous layer is separated, acidified with 10% hydrochloric acid and extracted with ethyl acetate. The extract is washed with an aqueous saline solution, dried and then distilled under reduced pressure to remove the solvent. The residue is purified by silica gel column chromatography (solvent, methanol:chloroform) and further recrystallized from ethyl acetate and isopropyl ether to give 5-[[2-[(4-chlorophenyl)sulfonylamino]indan-5-yl]acetylamino] -n-pentanoic acid (661 mg) as colorless solid.

m.p. 156°–157.5° C.
MS (m/e): 464 (M⁺)
IR $\nu_{max}^{nujol}$ cm⁻¹: 3320, 3260, 1690, 1640

EXAMPLE 49

In the same manner as described in Example 48, the corresponding starting compound is treated to give 6-[[2-[(4-chlorophenyl)sulfonylamino]indan-5-yl]acetylamino]-n-hexanoic acid.

m.p. 163°–164° C.
MS (m/e): 478 (M⁺)
IR $\nu_{max}^{nujol}$ cm⁻¹: 3280, 3170, 1710, 1620

EXAMPLE 50

(1) Methyl (-)-(2-aminoindan-5-yl)acetate.(−)-dibenzoyl-L-tartaric acid salt (3.94 g) is added to a mixture of potassium carbonate (4.83 g), water (50 ml) and ethyl acetate (70 ml), and 4-chlorophenylsulfonyl chloride (1.49 g) is added thereto. The mixture is stirred at room temperature for one hour. The ethyl acetate layer is separated from the reaction mixture, washed with an aqueous sodium hydrogen carbonate solution, dried, and distilled under reduced pressure to remove the solvent. The residue is recrystallized from a mixture of ethyl acetate and hexane to give methyl (-)-[2-[(4-chlorophenyl)sulfonylamino]indan-5-yl]acetate (2.43 g) as colorless crystals.

m.p. 80°-82° C.
IR $\nu_{max}^{nujol}$ (cm$^{-1}$): 3290, 3260, 1725
$[\alpha]_D^{20}$ −452° (c=1.017, CHCl$_3$)

(2) To a solution of the above product (1.14 g) in methanol (15 ml) is added 1N aqueous sodium hydroxide (6 ml), and the mixture is stirred at room temperature for 2 hours and distilled under reduced pressure to remove the solvent. The residue is acidified with 10% hydrochloric acid and extracted with ethyl acetate. The extract is dried and distilled under reduced pressure to remove the solvent. The resulting crude product is recrystallized from a mixture of ethyl acetate and hexane to give (−)-[2-[(4-chlorophenyl)sulfonylamino]indan-5-yl]acetic acid (0.94 g).

m.p. 154°-155° C.
IR $\nu_{max}^{nujol}$ (cm$^{-1}$): 1700
$[\alpha]_D^{20}$ −8.01° (c=0.512, methanol)

(3) The above product (1.098 g), thionyl chloride (2.4 ml), tetrahydrofuran (15 ml) and methylene chloride (15 ml) are mixed, and the mixture is refluxed with stirring for 3 hours. After the reaction, the solvent is distilled off under reduced pressure. The residue is dissolved in methylene chloride (15 ml), and the solution is added dropwise to a mixture of methyl 3-aminopropionate hydrochloride (837 mg), triethylamine (1.00 g) and methylene chloride (30 ml) under ice-cooling. After stirring the mixture at room temperature for 3 hours, the reaction mixture is distilled under reduced pressure to remove the solvent. Ethyl acetate and water are added to the residue, and the mixture is extracted with ethyl acetate. The extract is washed with 10% hydrochloric acid, saline solution and aqueous sodium bicarbonate solution in this order, dried and then distilled under reduced pressure to remove the solvent. The residue is recrystallized from a mixture of methanol, hexane and isopropyl ether to give methyl (−)-3-[[2-[(4-chlorophenyl)sulfonylamino]indan-5-yl]acetylamino]-n-propionate (1.138 g).

m.p. 110°-113° C.
IR $\nu_{max}^{nujol}$ (cm$^{-1}$): 3390, 3170, 1725, 1650
$[\alpha]_D^{20}$ −8.52° (c=0.563, methanol)

(4) A mixture of the above product (992 mg), 1N aqueous sodium hydroxide (4.4 ml) and methanol (8.8 ml) is stirred at room temperature for 2 hours. The mixture is acidified with 10% hydrochloric acid and extracted with ethyl acetate. The extract is washed with water, dried and distilled under reduced pressure to remove the solvent. The resulting crude crystals are recrystallized from a mixture of ethyl acetate and hexane to give (−)-3-[[2-[(4-chlorophenyl)sulfonylamino]indan-5-yl]acetylamino]-n-propionic acid (821 mg).

m.p. 141°-142° C.
IR $\nu_{max}^{nujol}$ (cm$^{-1}$): 3320, 3260, 1695, 1650
$[\alpha]_D^{20}$ −8.45° (c=0.201, methanol)

EXAMPLES 51 TO 53

(1) In the same manner as described in Examples 50-(1), methyl (+)-(2-aminoindan-5-yl)acetate (+)-dibenzoyl-D-tartaric acid salt and 4-chlorophenylsulfonyl chloride are treated to give methyl (+)-[2-[(4-chlorophenyl)sulfonylamino]indan-5-yl]acetate.

m.p. 80°-82° C.
IR $\nu_{max}^{nujol}$ (cm$^{-1}$): 3290, 3260, 1725
$[\alpha]_D^{20}$ +4.76° (c=1.049, CHCl$_3$)

(2) In the same manner as described in Example 50-(2), methyl (+)-[2-[(4-chlorophenyl)sulfonylamino]indan-5-yl]acetate is treated to give (+)-[2-[(4-chlorophenyl)sulfonylamino]indan-5-yl]acetic acid.

m.p. 154°-155° C.
IR $\nu_{max}^{nujol}$ (cm$^{-1}$): 1700
$[\alpha]_D^{20}$ +9.16° (c=0.513, methanol)

(3) In the same manner as described in Example 50-(3), (−)- or (+)-[2-[(4-chlorophenyl)sulfonylamino]indan-5-yl]acetic acid and methyl 3-aminopropionate or methyl 4-aminobutyrate are treated to give the following compounds.

(i) methyl (+)-3-[[2-[(4-chlorophenyl)sulfonylamino]indan-5-yl]acetylamino]-n-propionate
m.p. 110°-113° C.
IR $\nu_{max}^{nujol}$ (cm$^{-1}$): 3390, 3170, 1725, 1650
$[\alpha]_D^{20}$ +8.65° (c=0.566, methanol)

(ii) methyl (-)-4-[[2-[(4-chlorophenyl)sulfonylamino]indan-5-yl]acetylamino]-n-butyrate
m.p. 129.5°-130° C.
IR $\nu_{max}^{nujol}$ (cm$^{-1}$): 3300, 1730, 1640
$[\alpha]_D^{20}$ −8.56° (c=0.537, methanol)

(iii) methyl (+)-4-[[2-[(4-chlorophenyl)sulfonylamino]indan-5-yl]acetylamino]-n-butyrate
m.p. 129.5°-130° C.
IR $\nu_{max}^{nujol}$ (cm$^{-1}$): 3300, 1730, 1640
$[\alpha]_D^{20}$ +8.47° (c=0.531, methanol)

(4) In the same manner as described in Example 50-(4), the compounds obtained in Paragraph (3) are treated to give the following compounds.

(i) (+)-3-[[2-[(4-chlorophenyl)sulfonylamino]-indan-5-yl]acetylamino]-n-propionic acid
m.p. 141°-142° C.
IR $\nu_{max}^{nujol}$ (cm$^{-1}$): 3320, 3260, 1695, 1650
$[\alpha]_D^{20}$ +8.45° (c=0.201, methanol)

(ii) (-)-4-[[2-[(4-chlorophenyl)sulfonylamino]-indan-5-yl]acetylamino]-n-butyric acid
m.p. 129.5°-131° C.
IR $\nu_{max}^{nujol}$ (cm$^{-1}$): 3350, 3290, 1720
$[\alpha]_D^{20}$ −9.3° (c=0.473, tetrahydrofuran)

(iii) (+)-4-[[2-[(4-chlorophenyl)sulfonylamino]indan-5-yl]acetylamino]-n-butyric acid
m.p. 129.5°-131° C.
IR $\nu_{max}^{nujol}$ (cm$^{-1}$): 3350, 3290, 1720
$[\alpha]_D^{20}$ +9.33° (c=0.418, tetrahydrofuran)

EXAMPLE 54

[2-[(4-Chlorophenyl)sulfonylamino]indan-5-yl]acetic acid (600 mg) is dissolved in tetrahydrofuran (20 ml) and thereto is added dropwise 7.8M borane-1,4-oxathiane complex (1 ml). The mixture is stirred at room temperature for one hour and thereto is added methanol to terminate the reaction, and then, the solvent is distilled off under reduced pressure. The residue is dissolved in ethyl acetate and washed with aqueous sodium hydrogen carbonate solution and saline solution, dried and then distilled under reduced pressure to remove the solvent. The residue is purified by silica gel column chromatography (solvent, chloroform) to give 2-[2-[(4-chlorophenyl)sulfonylamino]indan-5-yl]ethanol (542 mg) as colorless crystals.

m.p. 71°-76° C.
MS (m/e): 351 (M$^+$)
IR $\nu_{max}^{nujol}$ (cm$^{-1}$): 3500, 3150 (broad)

REFERENCE EXAMPLE 1

(1) To a solution of 2-aminoindan (19.95 g) in tetrahydrofuran is added an solution of 2M acetic acid-formic acid anhydride in tetrahydrofuran under ice cooling, and the mixture is reacted at room temperature. To the reaction mixture is added water, and then, the solvent is distilled off, and the residue is extracted with ethyl acetate. After distilling off the solvent, the residue is recrystallized from ethyl acetate - n-hexane to give 2-formylaminoindan (19.02 g).

To a solution of the above product (3.22 g) and methyl chloro(methylthio)acetate (3.58 g) in methylene chloride is added dropwise a solution of tin (IV) chloride in methylene chloride under cooling, and the mixture is reacted at room temperature, and thereto is added water. The mixture is extracted with chloroform. The solvent is distilled off from the organic layer, and to the residue are added acetic acid and zinc dust, and the mixture is refluxed. After removing the zinc dust by filtration, the solvent is distilled off. The residue is extracted with ethyl acetate and the solvent is again distilled off to give ethyl (2-formylaminoindan-5-yl)acetate (4.31 g) as colorless oil.

IR $\nu_{max}^{nujol}$ (cm$^{-1}$): 3300, 1730, 1660

(2) To a solution of the above product (2.33 g) in methanol is added 1N aqueous sodium hydroxide, and the mixture is reacted at room temperature. The reaction mixture is neutralized with hydrochloric acid and extracted with ethyl acetate. The extract is distilled to remove the solvent, and the residue is recrystallized from ethyl acetate to give (2-formylaminoindan-5-yl)acetic acid (1.50 g).

m.p. 164°-166° C.

REFERENCE EXAMPLE 2

(2-Benzyloxycarbonylaminoindan-5-yl)acetic acid is obtained in the same manner as described in Reference Example 1 except that benzyloxycarbonyl chloride is used instead of 2M acetic acid-formic acid anhydride.

m.p. 157.5°-158.5° C.

REFERENCE EXAMPLE 3

(1) To a solution of phenylthioacetic acid (8.14 g) in a mixture of methylene chloride-tetrahydrofuran is added carbonyldiimidazole under ice cooling and the mixture is stirred, and to the reaction mixture are added β-alanine methyl ester hydrochloride (6.98 g) and triethylamine, and the mixture is reacted. After the reaction, the solvent is distilled off under reduced pressure. The residue is extracted with ethyl acetate. The extract is distilled to remove the solvent, and the residue is recrystallized from ethyl acetate - n-hexane to give methyl 3-[(phenylthio)-acetylamino]-n-propionate (10.95 g).

m.p. 62°-63° C.

(2) To a solution of the above product (6.35 g) in methylene chloride is added N-chlorosuccinimide (3.50 g), and the mixture is reacted. After the reaction, the solvent is distilled off, and to the residue is added carbon tetrachloride, and the mixture is filtered. The filtrate is concentrated, and the residue is recrystallized from n-hexane to give methyl 3-[chloro(phenylthio)acetylamino]-n-propionate (7.12 g).

m.p. 49°-52° C.

REFERENCE EXAMPLE 4

Methyl 4-[chloro(phenylthio)acetylamino]-n-butyrate is obtained in the same manner as described in Reference Example 3 except that methyl 4-aminobutyrate is used instead of β-alanine methyl ester.

m.p. 38°-40° C.

REFERENCE EXAMPLE 5

(1) To a mixture of 2-aminoindan hydrochloride (10.40 g), potassium carbonate (34.2 g), water (100 ml) and ethyl acetate (150 ml) is added dropwise acetyl chloride (9.68 g) under ice cooling. The mixture is stirred at 0° C. for 1.5 hour, and the ethyl acetate layer is separated, washed with aqueous saline solution, dried, and then the solvent is distilled off under reduced pressure. The residue is recrystallized from ethyl acetate - n-hexane to give 2-acetylaminoindan (9.5 g) as colorless crystals. m.p. 126.5°-127.5° C.

(2) To a mixture of the above product (13.06 g), ethyl chloro(methylthio)acetate (13.35 g) and methylene chloride (100 ml) is added dropwise a solution of stannic chloride (40.0 g) in methylene chloride (50 ml) under ice cooling. The mixture is stirred at 0° C. to room temperature for 2 hours, and the reaction mixture is poured onto ice and then extracted with ethyl acetate. The extract is washed with 10% hydrochloric acid, aqueous sodium hydrogen carbonate solution and aqueous saline solution in this order, dried, and then distilled under reduced pressure to remove the solvent. The residue (24.3 g) is dissolved in acetic acid (150 ml) and thereto is added zinc dust (100 g), and the mixture is refluxed for 2 hours. After cooling, the mixture is filtered, and the filtrate is concentrated under reduced pressure, and then, acetic acid is distilled off. To the residue are added water and ethyl acetate, and the ethyl acetate layer is separated, washed with aqueous sodium hydrogen carbonate solution and aqueous saline solution, dried and distilled under reduced pressure to remove the solvent. The crude crystals thus obtained are recrystallized from diethyl ether - n-hexane to give ethyl (2-acetylaminoindan-5-yl)acetate (15.67 g) as colorless crystals. m.p. 82°-84° C.

(3) A mixture of the above product (16.69 g) and 2N hydrochloric acid (100 ml) is refluxed for 18 hours. After the reaction, the solvent is distilled off under reduced pressure. Methanol (100 ml) is added to the residue and the mixture is refluxed for one hour. After cooling, the solvent distilled off under reduced pressure. The crude crystals thus obtained are recrystallized from a mixture of methanol, isopropanol and isopropyl ether to give methyl (2-aminoindan-5-yl)acetate (15.14 g) as colorless crystals.

m.p. 145°-148° C.

(4) Methyl (2-aminoindan-5-yl)acetate (10.89 g) is added to 1N aqueous sodium bicarbonate solution (200 ml), and the mixture is extracted with chloroform. The extract is dried and distilled under reduced pressure to remove the solvent. The residue is dissolved in 90% aqueous methanol (300 ml) and thereto is added a solution of (−)-dibenzoyl-L-tartaric acid hydrate (16.93 g) in 90% aqueous methanol (200 ml). The mixture is allowed to stand for 2 days, and the resulting crude crystals are recrystallized from 90% aqueous methanol to give methyl (−)-(2-aminoindan-5-yl)acetate.(-)-dibenzoyl-L-tartaric acid salt (4.71 g).

m.p. 184°-184.5° C.

$[\alpha]_D^{20}$ −79.2° (c=0.202, 50% methanol)

The mother liquor obtained above is distilled under reduced pressure to remove the solvent, and to the residue are added water (200 ml) and potassium carbonate (11.75 g). The mixture is extracted with chloroform, and the extract is dried and distilled under reduced pressure to remove the solvent. The residue is dissolved in 90% aqueous methanol and thereto is added a solution of (+)-dibenzoyl-D-tartaric acid hydrate (10.60 g) in 90% aqueous methanol. The mixture is allowed to stand, and the resulting crude crystals are recrystallized from 90% aqueous methanol to give methyl (+)-(2-aminoindan-5-yl)-acetate.(+)-dibenzoyl-D-tartaric acid salt (5.12 g).

m.p. 184°–184.5° C.
$[\alpha]_D^{20} + 79.51°$ (c=0.205, 50% methanol)

EXPERIMENTS (1) Effect on bronchoconstriction (in vivo)

Hartley-male guinea pigs were anesthetized with α-chloralose (120 mg/kg, i.v.), and a tracheal cannula was inserted to each of the guinea pigs. Each one of the guinea pigs was immobilized by administration of gallamine triethiotide (5 mg/kg, i.v.) under artificial respiration (ca. 1.0 ml/100 g, 60 strokes/min). The volume of the artificial respiration was regulated so that the peak of intratracheal pressure (ITP) was ca. 10 cm H$_2$O. The change of ITP was measured by a pressure-transducer connected to the tracheal cannula. After 0.3, 0.7 and 2 μg/kg of U-46619 (11,9-epoxymethano-PGH$_2$) were administered to each of the guinea pigs intravenously (or intraduodenally) at 30-minute intervals and the reaction of administration of U-46619 was stabilized, the solution of a test compound in physiological saline was administered to lateral saphenous vein of the guinea pig five minutes before administration of U-46619, and the change of the ITP was measured. The Inhibition was calculated according to the following formula.

Inhibition (%) =

$$\frac{\left(\begin{array}{c}\text{change (cm H}_2\text{O)}\\\text{of ITP obtained by}\\\text{administration}\\\text{of U-46619}\end{array}\right) - \left(\begin{array}{c}\text{change (cm H}_2\text{O) of ITP}\\\text{obtained by administration}\\\text{of a test compound}\end{array}\right)}{\text{change (cm H}_2\text{O) of ITP obtained by}\\\text{administration of U-46619}} \times 100$$

The results are shown in Table 1.

TABLE 1

| Administration route | administration dose (mg/kg) | Inhibition (%) | ED$_{50}$ (mg/kg) |
|---|---|---|---|
| intravenously | 0.3 | 12 | 0.62 |
|  | 1 | 78 |  |
|  | 3 | 100 |  |
| intraduodenally | 3 | 49 | 3 |
|  | 10 | 70 |  |

(2) Effect on bronchoconstriction (in vivo)

Hartley-male guinea pigs were anesthetized with α-chloralose (120 mg/kg, i.v.), and a tracheal cannula was inserted to each of the guinea pigs. Each one of the guinea pigs was immobilized by administration of gallamine triethiotide (5 mg/kg, i.v.) under artificial respiration (ca. 1.0 ml/100 g, 60 strokes/min). The volume of the artificial respiration was regulated so that the peak of intratracheal pressure (ITP) was ca. 10 cm H$_2$O. The change of ITP was measured 150 minutes after administration of the test compounds by a pressure-transducer connected to the tracheal cannula. After 30 μg/kg of PGD$_2$ were administered to each of the guinea pigs intravenously at 30-minute intervals and the reaction of administration of PGD$_2$ was stabilized, the solution of a test compound in physiological saline was administered to lateral saphenous vein of the guinea pig, and the change of the ITP was measured. The Inhibition was calculated according to the following formula.

Inhibition (%) =

$$\frac{\left(\begin{array}{c}\text{change (cm H}_2\text{O)}\\\text{of ITP obtained by}\\\text{administration}\\\text{of PGD}_2\end{array}\right) - \left(\begin{array}{c}\text{change (cm H}_2\text{O) of ITP}\\\text{obtained by administration}\\\text{of a test compound}\end{array}\right)}{\text{change (cm H}_2\text{O) of ITP obtained by}\\\text{administration of PGD}_2} \times 100$$

The results are shown in Table 2.

TABLE 2

| Administration route | administration dose (mg/kg) | Inhibition (%) | ED$_{50}$ (mg/kg) |
|---|---|---|---|
| intravenously | 0.1 | 40 | 0.17 |
|  | 0.3 | 70 |  |
|  | 1 | 80 |  |
|  | 3 | 85 |  |

(3) Effect on antigen-induced bronchoconstriction

Hartley-male guinea pigs were passively sensitized by intravenous injection of rabbit antiserum against ovalbumin (0.1 ml/100 g of body weight). 24 hours later, the animals were anesthetized with α-chloralose (120 mg/kg, i.v.), and after a tracheal cannula was inserted to them, the animals were immobilized by administration of gallamine triethiotide (5 mg/kg, i.v.) under artificial respiration (ca. 1.0 ml/100 g, 60 strokes/min). Lung volume changes were measured as overflow of air from the lung by the modified Konzett-Rössler method (cf. Arch. Exp. pathol. Pharmakol., 195, 71 (1940)). The test compound was administered intravenously (or orally) to the animals five minutes before said animals were challenged with an antigen (ovalbumin, 30 μg/kg, i.v.). Mepyramine was administered to the animals 10 minutes before said animals was administered the antigen.

The bronchoconstriction was estimated by comparing the increase in ventilation overflow volume by an artificial blockade of a trachea and that by an administration of an antigen. The inhibitory effect of a test compound was calculated according to the following formula.

Inhibition (%) =

$$\frac{\left(\begin{array}{c}\text{bronchoconstriction}\\(\%) \text{ of the}\\\text{control group}\end{array}\right) - \left(\begin{array}{c}\text{bronchoconstriction (\%)}\\\text{of the group administered}\\\text{the test compound}\end{array}\right)}{\text{bronchoconstriction (\%)}\\\text{of the control group}} \times 100$$

The results are shown in Table 3.

TABLE 3

| Administration route | administration dose (mg/kg) | Inhibition (%) |
|---|---|---|
| intravenously | 10 | 70 |
| orally | 100 | 67 |

(4) Effect on bronchoconstriction (in vivo)

Male and female dogs were anesthetized with sodium pentobarbital (PB: 30 mg/kg, i.v.), and a tracheal cannula was inserted to each of the dogs. After thoracotomy, the following experiment was carried out under artificial respiration (ca. 1.0 ml/100 g, 60 strokes/min).

The volume of the artificial respiration was regulated so that the peak of intratracheal pressure (ITP) was ca. 10 cm $H_2O$. The change of ITP was measured by a pressure-transducer connected to the tracheal cannula. After 0.3, 0.7 and 2 μg/kg of U-46619 were administered to each of the guinea pigs intravenously (or intraduodenally) at 30-minute intervals and the reaction of administration of U-46619 was stabilized, the solution of a test compound in physiological saline was administered to lateral saphenous vein of the guinea pig five minutes before administration of U-46619, and the change of the ITP was measured. The Inhibition was calculated according to the following formula.

Inhibition (%) =

$$\frac{\left(\begin{array}{c}\text{change (cm } H_2O)\\ \text{of ITP obtained by}\\ \text{administration}\\ \text{of U-46619}\end{array}\right) - \left(\begin{array}{c}\text{change (cm } H_2O) \text{ of ITP}\\ \text{obtained by administration}\\ \text{of a test compound}\end{array}\right)}{\text{change (cm } H_2O) \text{ of ITP obtained by}\\ \text{administration of U-46619}} \times 100$$

The results are shown in Table 4.

TABLE 4

| Administration route | administration dose (mg/Kg) | Inhibition (%) | $ED_{50}$ (mg/kg) |
|---|---|---|---|
| intravenously | 0.03 | 20 | 0.11 |
| | 0.1 | 50 | |
| | 0.2 | 80 | |
| | 1 | 95 | |
| | 3 | 100 | |
| | 10 | 100 | |
| intraduodenally | 0.3 | 80 | — |

What is claimed is:

1. A method for the treatment or prophylaxis of thromboses in a warm-blooded animal which comprises administering an effective amount of a compound having the formula:

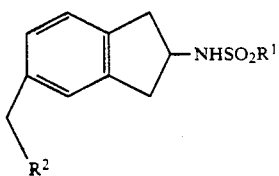

wherein $R^1$ is a phenyl group or a phenyl group substituted by a member selected from the group consisting of a $C_1-C_5$ alkyl group, a $C_1-C_5$ alkoxy group, a halogen atom, trifluoromethyl, and nitro, or a naphthyl group, and $R^2$ is a hydroxymethyl group or a group of the formula:

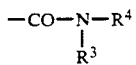

wherein $R^3$ is hydrogen atom or a $C_1-C_5$ alkyl group and $R^4$ is a $C_3-C_6$ cycloalkyl group, a $C_2-C_6$ alkoxycarbonyl-phenyl group, carboxy-phenyl group, a $C_1-C_5$ alkyl group, or a $C_1-C_5$ alkyl group having a substituent selected from a $C_1-C_5$ alkoxycarbonyl group, carboxy group, a $C_2-C_6$ alkoxycarbonylphenyl group, a carboxy-phenyl group, a $C_2-C_6$ alkoxycarbonyl-($C_3-C_6$)cycloalkyl group and a carboxy-($C_3-C_6$)cycloalkyl group, or a pharmaceutically acceptable salt thereof to said warm blooded animal.

2. The method according to claim 1, wherein in said compound, $R^1$ is chlorophenyl, and $R^4$ is carboxyphenyl or a $C_1-C_4$ alkyl substituted by a carboxy, or a pharmaceutically acceptable salt thereof.

3. A method for the treatment or prophylaxis of asthma in a warm-blooded animal which comprises administering an effective amount of a compound having the formula:

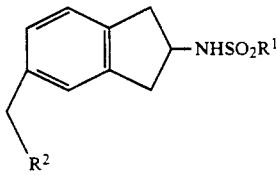

wherein $R^1$ is a phenyl group or a phenyl group substituted by a member selected from the group consisting of a $C_1-C_5$ alkyl group, a $C_1-C_5$ alkoxy group, a halogen atom, trifluoromethyl, and nitro, or a naphthyl group, and $R^2$ is a hydroxymethyl group or a group of the formula:

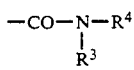

wherein $R^3$ is a hydrogen atom or a $C_1-C_5$ alkyl group and $R^4$ is a $C_3-C_6$ cycloalkyl group, a $C_2-C_6$ alkoxycarbonyl-phenyl group, carboxy-phenyl group, a $C_1-C_5$ alkyl group, or a $C_1-C_5$ alkyl group having a substituent selected from a $C_1-C_5$ alkoxycarbonyl group, carboxy group, a $C_2-C_6$ alkoxycarbonylphenyl group, a carboxy-phenyl group, a $C_2-C_6$ alkoxycarbonyl-($C_3-C_6$)cycloalkyl group and a carboxy-($C_3-C_6$)cycloalkyl group, or a pharmaceutically acceptable salt thereof to said warm blooded animal.

4. The method according to claim 3, wherein in said compound, $R^1$ is chlorophenyl, and $R^4$ is carboxyphenyl or a $C_1-C_4$ alkyl substituted by a carboxy, or a pharmaceutically acceptable salt thereof.

* * * * *